(12) United States Patent
Chen et al.

(10) Patent No.: US 6,620,597 B1
(45) Date of Patent: Sep. 16, 2003

(54) METHOD FOR IN VITRO AMPLIFICATION OF CIRCULAR DNA

(75) Inventors: Zhidong Chen, Salt Lake City, UT (US); Duane E. Ruffner, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/582,906

(22) PCT Filed: Jan. 9, 1999

(86) PCT No.: PCT/US99/00455

§ 371 (c)(1), (2), (4) Date: Jul. 6, 2000

(87) PCT Pub. No.: WO99/35281

PCT Pub. Date: Jul. 15, 1999

Related U.S. Application Data

(60) Provisional application No. 60/071,101, filed on Jan. 9, 1998.

(51) Int. Cl.$^7$ .............................. C12Q 1/68; C12P 19/34; C12N 9/00; C12N 15/87; C12N 15/00
(52) U.S. Cl. ..................... 435/91.1; 435/91.2; 435/183; 435/475; 435/462; 435/440; 435/6; 435/91.52; 435/91.51
(58) Field of Search ........................... 435/6, 91.2, 183, 435/475, 462, 440, 91.52, 91.51, 91.1

(56) References Cited

U.S. PATENT DOCUMENTS

| | | | |
|---|---|---|---|
| 5,354,656 A | | 10/1994 | Sorge et al. ............... 435/6 |
| 5,514,568 A | | 5/1996 | Stemmer ................. 435/91.2 |
| 5,523,221 A | * | 6/1996 | Weiner ................... 435/172.3 |
| 5,545,552 A | | 8/1996 | Mathur ................... 435/252.3 |
| 5,561,058 A | * | 10/1996 | Gelfand et al. ............ 435/91.2 |
| 5,658,751 A | | 8/1997 | Yue et al. ................. 435/34 |
| 5,932,419 A | * | 8/1999 | Bauer et al. ................. 435/6 |

FOREIGN PATENT DOCUMENTS

| | | | |
|---|---|---|---|
| EP | 0 439 182 A2 | 7/1991 | ............ C12Q/1/68 |
| WO | WO 93/12257 | 6/1993 | ............ C12Q/1/68 |

OTHER PUBLICATIONS

Zoller, New recombinant DNA methodology protein engineering, Biotechnology, 1992, vol. 3, p. 348–354.*
Barany, F. "Genetic disease detection and DNA amplification using cloned thermostable ligase," Proceedings of the National Academy of Sciences of the USA, National Academy of Sciences. Washington, US, vol. 88, No. 1, 1991, pp. 189–193.
Chen, Z. et al. "Amplification of closed circular DNA in vitro," Nucleic Acids Research, Oxford University Press, Surrey, GB, vol. 26, No. 4, Dec. 1, 1998, pp. 1126–1127.
Jones, D.H. et al. "Recombinant Circle PCR and Recombination PCR for Site–Specific Mutagenesis Without PCR Product Purification," Biotechniques, Eaton Publishing, Natick, US, vol. 12, No. 4, 1992, pp. 528–530, 532, 534–535.

* cited by examiner

*Primary Examiner*—Kenneth R. Horlick
*Assistant Examiner*—Joyce Tung
(74) *Attorney, Agent, or Firm*—Clayton, Howarth & Cannon, P.C.

(57) ABSTRACT

A method for generating and amplifying closed circular DNA having a specific sequence in vitro in a cell-free system is disclosed. Prior to the invention of this method, closed circular DNA could only be amplified in vivo in appropriate host cells. The essence of the method is the inclusion of a thermostable DNA ligase in a PCR reaction. This procedure is referred to as ligation-during-amplification (LDA), in which the fully extended DNA strands are ligated by the DNA ligase and used as templates for subsequent amplification. Closed circular DNA having a specific sequence can be selectively amplified exponentially by the use of two sequence-specific primers in the LDA reaction. In addition, one or more site-specific mutations can be introduced into a closed circular DNA by the use of one or more mutagenic primers in the LDA reaction. Various thermostable DNA polymerases and thermostable ligases can be used for LDA amplification. Any primer position and orientation, either inward or outward, can be used in LDA amplification, as long as there is at least one primer complementary to each strand of the circular DNA. This method has applications in the areas of mutagenesis, cloning, DNA detection, DNA modification, gene hunting, gene therapy, and cell-free DNA production.

29 Claims, 2 Drawing Sheets

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: PCR primer

<400> SEQUENCE: 1
ggcaaaagaa gcgcagaatt tcg                        23

<210> SEQ ID NO 2
<211> LENGTH: 18
<212> TYPE: DNA
<213> ORGANISM: Artificial Sequence
<220> FEATURE:
<223> OTHER INFORMATION: PCR primer

<400> SEQUENCE: 2
cgtggtatgc gttacacc                              18

METHOD FOR IN VITRO AMPLIFICATION OF CIRCULAR DNA

CROSS-REFERENCE TO RELATED APPLICATION

This application claims the benefit of U.S. Provisional Application No. 60/071,101, filed Jan. 9, 1998.

STATEMENT REGARDING FEDERALLY SPONSORED RESEARCH OR DEVELOPMENT

This invention was made with government support under Grant No. 5R29AI34278-01A2 awarded by the National Institutes of Health. The government has certain rights in the invention.

BACKGROUND OF THE INVENTION

This invention relates to a method for the in vitro amplification of closed circular DNA. More particularly, the invention relates to a process for the cell-free amplification of closed circular DNA for applications such as mutagenesis, molecular cloning, DNA detection, DNA modification, gene hunting, gene therapy, and cell-free DNA production.

The polymerase chain reaction (PCR) is a powerful method for the rapid and exponential amplification of target nucleic acids. E.g., U.S. Pat. Nos. 4,683,195 and 4,683,202, hereby incorporated by reference. PCR has facilitated the development of gene characterization and molecular cloning technologies including direct sequencing of PCR-amplified DNA, the determination of allelic variation, and the detection of infectious and genetic disorders. PCR is performed by repeated cycles of heat denaturation of a DNA template containing the target sequence, annealing of opposing primers to the complementary DNA strands, and extension of the annealed primers with a DNA polymerase. Multiple PCR cycles result in the exponential amplification of the nucleotide sequence delineated by the flanking amplification primers.

An important modification of the original PCR technique was the substitution of *Thermus aquaticus* (*Taq*) DNA polymerase in place of the Klenow fragment of *E. coil* DNA polymerase I. Saiki et al., 230 Science 1350–1354 (1988). The incorporation of a thermostable DNA polymerase into the PCR protocol obviates the need for repeated enzyme additions and permits elevated annealing and primer extension temperatures, which enhance the specificity of primer/template associations. Other thermostable DNA polymerases have also been discovered and commercialized, such as the thermostable DNA polymerase from *Pyrococcus furiosus* (*Pfu* DNA polymerase; U.S. Pat. No. 5,545,552, hereby incorporated by reference), the thermostable DNA polymerase from *Thermus flavus* (*Tfl* DNA polymerase; Epicentre Technologies), the thermostable DNA polymerase from *Thermus thermophilus* (*Tth* DNA polymerase, Epicentre Technoloigies, Madison, Wis.), a mixture of *Taq* DNA polymerase and *Pyrococcus species* GB-D thermostable DNA polymerase (ELONGASE™, Life Technologies, Inc., Gaithersburg, Md.), the thermostable DNA polymerase from *Thermococcus litoralis* (Vent$_R$® DNA polymerase, New England Biolabs, Beverly, Mass.), and AMPLITHERM™ DNA polymerase (proprietary thermostable DNA polymerase, Epicentre Technologies). Thermostable DNA polymerases thus serve to increase the specificity and simplicity of PCR. PCR can be used to amplify linear DNA segments, but not closed circular DNA. Since most replicatively competent DNAs exist in closed circular form, for functional studies a PCR product needs to be subcloned into a closed circular DNA vector and then introduced into and amplified in appropriate cellular hosts. The ability to amplify circular DNA in vitro in a cell-free system would allow modification of the nucleotide composition and sequence of a circular DNA at will. This achievement would represent a significant advancement in the art and have potential applications in areas of mutagenesis, cloning, DNA detection, DNA modification, gene hunting, gene therapy, and cell-free DNA production.

BRIEF SUMMARY OF THE INVENTION

It is an object of the present invention to provide a method of producing and amplifying closed circular DNA in vitro.

It is another object of the invention to provide a method of modifying the nucleotide composition and sequence of a closed circular DNA and amplifying the modified closed circular DNA in vitro.

It is still another object of the invention to provide a method of selectively amplifying a closed circular DNA having a defined nucleotide sequence in vitro.

These and other objects can be addressed by providing a method for in vitro amplification of a selected closed circular DNA comprising:

(a) mixing an effective amount of a thermostable DNA ligase with a PCR reaction mixture comprising the selected closed circular DNA as a template and a pair of 5'-phosphorylated amplification primers, with the proviso that any cofactor required for activity of the thermostable DNA ligase is also added in an effective amount, to result in an LDA mixture; and (b) thermocycling the LDA mixture through a selected number of cycles of (i) a temperature suitable for denaturing the template, (ii) a temperature suitable for annealing the primers to the denatured template, (iii) a temperature suitable for polymerase-catalyzed extension of the primers, and (iv) a temperature suitable for ligase-catalyzed closing of the extended primers to result in an amplified closed circular DNA product.

In one illustrative embodiment of the invention, the temperature suitable for polymerase-catalyzed extension of the primers is the same as the temperature suitable for ligase-catalyzed closing of the extended primers. The temperature suitable for annealing the primers to the denatured template can also be the same as the temperature suitable for polymerase-catalyzed extension of the primers.

In preferred embodiments, the LDA mixture is held at the temperature suitable for denaturing the template for about 1 second to about 2 minutes in each cycle; the LDA mixture is held at the temperature suitable for annealing the primers to the denatured template for about 1 second to about 5 minutes in each cycle; and the LDA mixture is held at the temperature suitable for polymerase-catalyzed extension of the primers for about 1 to 20 minutes in each cycle.

When at least one of the primers has at least one mismatch with its corresponding template strand, the resulting amplified closed circular DNA product comprises a mutation as compared to the template. When at least one of the primers hybridizes to its corresponding template strand across a cloning site for an insert in a cloning vector, the resulting amplified closed circular DNA is in one orientation of the insert in the cloning vector. When the PCR reaction mixture further comprises a modified nucleotide, the amplified closed circular DNA product comprises the modified nucleotide residue incorporated randomly therein. When at least one of the primers comprises a modified nucleotide, the amplified closed circular DNA product has the modified nucleotide residue incorporated at a pre-selected site.

DETAILED DESCRIPTION

Figure 1:
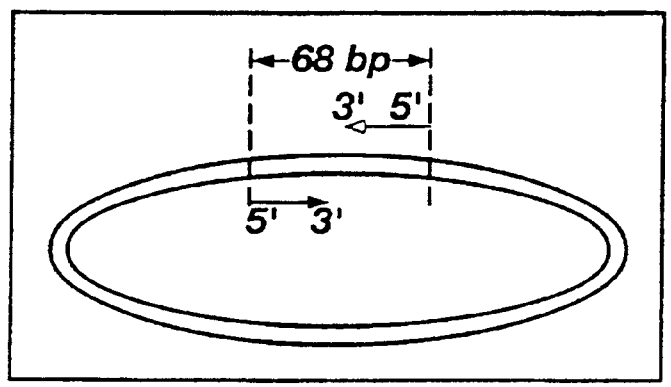
FIG. 1 shows a preferred primer configuration for amplification of closed circular DNA according to the present invention.

Before the present method for producing and amplifying closed circular DNA iii vitro in a cell-free system is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a reaction mixture containing "a thermostable DNA ligase" includes a mixture of two or more of such thermostable ligases, reference to "a thermostable DNA polymerase" includes reference to one or more of such polymerases, and reference to "a template" includes reference to a mixture of two or more templates.

In describing and claiming the present invention, the following terminology will be used in accordance with the definitions set out herein.

As used herein, "ligation-during-amplification," "LDA," and similar terms mean a process comprising use of a thermostable DNA ligase in a PCR reaction under conditions that permit the production and amplification of closed circular DNA. That is, the reaction conditions permit both the extension of the primers and the ligation of adjacent 5'-phosphate groups and 3'-hydroxyl groups to form phosphodiester bonds, thus closing the circular DNA. It will be recognized by a person of ordinary skill in the art that the 5'-phosphate groups will ordinarily by provided from 5'-phosphorylated primers. As is well known in the art, these 5'-phosphate groups can be added to primers by a reaction catalyzed by T4 polynucleotide kinase, e.g. J. Sambrook et al., Molecular Cloning 10-59-10.67, 11.31–11.33 ($2^{nd}$ ed., 1989), or at the time of primer synthesis.

As used herein, "polymerase chain reaction" or "PCR" means a process such as is described in U.S. Pat. No. 4,683,195 and U.S. Pat. No. 4,683,202 for the amplification of a linear segment of DNA using at least two primers and a DNA polymerase. As currently practiced, such a polymerase would be a thermostable enzyme.

As used herein, "PCR reaction mixture" means a mixture suitable for carrying out PCR. The PCR reaction mixture will contain a suitable amount of a thermostable DNA polymerase, a template DNA (preferably double-stranded) for being amplified, a pair of primers such that one of the primers is configured for annealing to one strand of the template and the other primer is configured for annealing to the other or complementary strand of the template, ATP, suitable amounts of each of the four deoxyribonucleoside triphosphates (dNTPs), and buffers, salts, preservatives, reducing agents, and water as may be required.

As used herein, "thermostable DNA ligase" means any DNA ligase that maintains its activity for ligating DNA after being exposed to a plurality of cycles of thermocycling as would occur in a polymerase chain reaction or PCR. PCR is normally carried out by repeated cycling of the reaction mixture between temperature conditions for melting or denaturation of double-stranded template DNA (usually about 95° C.), annealing of primers to the melted (i.e. single-stranded) template DNA (usually about 50° C.), and elongating the annealed primers by primer extension (usually about 72° C.). The thermostable DNA polymerases typically used in PCR survive these cycles of temperature change. For example, *Thermus aquaticus* DNA polymerase (*Taq* DNA polymerase) is a thermostable enzyme that replicates DNA at 74° C., A. Chien et al., 127 J. Bacteriol. 1550 (1976); A. S. Kaledin et al., 45 Biokhimiya 494 (1980), and remains functional even after incubation at 95° C. For example, U.S. Pat. No. 4,889,818, hereby incorporated by reference, describes a purified thermostable DNA polymerase isolated from *Thermos aquaticus*. Thermostable DNA ligases are also well known in the art and are commercially available. For example, a thermostable DNA ligase from *Pyrococcus furiosus* (*Pfu* DNA ligase; U.S. Pat. Nos. 5,506,137 and 5,700,672, hereby incorporated by reference) is available from Stratagene (La Jolla, Calif.). This enzyme catalyzes the linkage of adjacent 5'-phosphate and 3'-hydroxy ends of double-stranded DNA at about 45° C. to 80° C. The enzyme is highly thermostable, having a half-life of greater than 60 minutes at 95° C., and the temperature optimum for nick-sealing reactions is about 70° C. By way of further example, *Taq* DNA ligase (from *Thermus aquaticus*) catalyzes the formation of a phosphodiester bond between juxtaposed 5'-phosphate and 3'-hydroxyl termini of two adjacent oligonucleotides that are hybrized to a complementary DNA. *Taq* DNA ligase is active at elevated temperatures (45° C. to 65° C.). F. Barany, 88 Proc. Nat'l Acad. Sci. USA 189 (1991); M. Takahashi et al., 259 J. Biol. Chem. 10041–10047 (1984). By way of still further example, AMPLIGASE® thermostable DNA ligase (Epicentre Technologies) catalyzes NAD-dependent ligation of adjacent 5'-phosphorylated and 3'-hydroxylated termini in duplex DNA structures. This enzyme has a half-life of 48 hours at 65° C. and greater than 1 hour at 95° C. This thermostable DNA ligase has also been shown to be active for at least 500 thermal cycles (94° C./80° C.) or 16 hours of cycling. M. Schalling et al., 4 Nature Genetics 135 (1993).

It will be recognized that many enzymes including polymerases and ligases require cofactors for activity. For example, *Taq* DNA ligase requires $NAD^+$ as a cofactor.

Therefore, a reaction catalyzed by *Taq* DNA ligase will require an appropriate amount of NAD$^+$ being added to the reaction mixture.

As used herein, "temperature suitable for denaturing the template" means a temperature at which the template is melted or denatured in view of the conditions present in the reaction mixture that are know to affect melting of nucleic acids, such as strandedness, monovalent cation concentration, GC content, length of the nucleic acid, presence or absence of mismatches, and concentration of certain solvents that affect melting. These factors are well known in the art, as are empirical formulas for determining thermal melting temperatures under selected conditions. A temperature above the thermal melting temperature ($T_m$) of the template will be selected. Denaturation temperatures of about 95° C. are typical.

As used herein, "temperature suitable for annealing the primers to the denatured template" means a temperature at which the single-stranded primers will anneal by hybridization to the denatured (single-stranded) template nucleic acid. The same factors that affect denaturation also affect annealing. Since the primers are typically in the range of about 10–30 nucleotide residues in length as opposed to templates that are usually thousands of nucleotide residues in length, and since thermal melting temperatures of short nucleic acids are lower than for longer nucleic acids, the annealing temperature will be well below the thermal melting temperature of the template. A temperature of about 40–50° C. is typical.

As used herein, "temperature suitable for polymerase-catalyzed extension of the primers" means a temperature at which the thermostable DNA polymerase is active. Preferably, the temperature is near the temperature optimum of the enzyme. For example, the *Thermococcus litoralis* DNA polymerase is maximally active at about 72–80° C. This is typical of thermostable polymerases.

As used herein, "temperature suitable for ligase-catalyzed closing of the extended primers" means a temperature at which the thermostable DNA ligase is active. Preferably, this temperature is near the temperature optimum of the enzyme and can be the same temperature selected for carrying out the polymerase-catalyzed extension reaction.

One illustrative method of using LDA to alter the nucleotide composition and sequence of a circular DNA and to selectively amplify the sequence-mutated closed circular DNA in vitro comprises the following steps:

(a) mixing the closed circular DNA, either single-stranded or double-stranded, to be mutated and/or amplified with the 5'phosphorylated primers, deoxyribonucleotides, thermostable DNA polymerase, thermostable DNA ligase, and a reaction buffer that supports the activity of both the polymerase and the ligase; and (b) subjecting the mixture to thermal cycles of DNA denaturation around 90° C., primer annealing around 50° C., primer extension and ligation around 70° C. to generate and amplify the closed circular DNA.

A major application of the present method is to introduce sited-directed mutagenesis into closed circular DNAs. By the use of one or multiple mutagenic primers in the LDA reaction, a circular DNA can be readily mutated and amplified. LDA-mediated mutagenesis has clear advantages over other mutagenesis methods In PCR-based mutagenesis, e.g. E. Merino et al., A General PCR-Based Method for Single or Combinatorial Oligonucleotide-Directed Mutagenesis on pUC/M13 Vectors, 12 Bio/Techniques 508–510 (1992), the sequence to be mutated is first amplified using mutagenic primers. The mutated DNA fragment is then purified. Subsequently, the native sequence in the original vector is substituted with the mutated fragment by subcloning. LDA-mediated mutagenesis does not require subcloning, and the mutated plasmid is amplified and used to transform a bacterial host directly. Therefore, it is a much simpler, easier, and faster method for the site-directed mutagenesis.

Combining PCR with a thermostable DNA ligase for site-directed mutagenesis has been reported. E.g., S. F. Michael, Thermostable Ligase-Mediated Incorporation of Mutagenic Oligonucleotides During PCT Amplification, in PCR Cloning Protocols: From Molecular Cloning to Genetic Engineering 189–195 (B. A. White ed., 1997). In this method, a thermostable DNA ligase and a mutagenic oligonucleotide complementary to a region within a PCR product are included in the PCR reaction. During PCR, the ligase incorporates the mutagenic primer into the PCR product. The mutation-containing PCR product is then purified and subcloned into the native plasmid as other PCR-based methods. Apparently the author did not envision the possibility of using thermostable ligase and PCR to generate and amplify closed circular DNA.

There are many commercially available site-directed mutagenesis methods. For example, the MORPH™ method of 5Prime→3Prime, Inc. (Boulder, Colo., catalog No. 1-205387), uses a mutagenic primer, T4 DNA polymerase, and T4 DNA ligase (a non-thermostable enzyme) to copy one of the two strands of a plasmid to form a "half-mutated" plasmid. The mutated plasmid needs to be selected in an *E. coli* mutS strain, which does not preferably select the native strand for plasmid propagation. LDA mutated plasmid does not have this limitation, because both DNA strands are mutated and thus the plasmid can be maintained in a non-mutS strain. The Unique Site Elimination (U.S.E.) method of Pharmacia Biotech Inc. (Piscataway, N.J. catalog No. 27-1699-01) uses two mutagenic primers that are complementary to the same strand of the plasmid to introduce mutations. W. P. Deng & J. A. Nickoloff, 200 Anal. Biochem. 81 (1992). One primer mutates the target site, and another primer mutates a unique restriction site. After a "half-mutated" plasmid is generated with T4 DNA polymerase and T4 DNA ligase, the mutated plasmid has to be enriched by digestion with the restriction enzyme and selected by sequential transformation into mutS and non-mutS bacterial strains. The ALTERED SITES® II method of Promega Corp (Madison, Wis., catalog No. Q6210) uses a similar approach. It requires a specialized plasmid, however, that has a premutated and inactivated antibiotic resistance gene. In this method, a "half-mutated" plasmid is similarly prepared with the use of a mutagenic primer complementary to the target sequence and another mutagenic primer to correct the premutated antibiotic resistance gene. The mutated plasmid is then transformed sequentially into mutS and non-mutS bacterial strains and selected by the rescued antibiotic resistance. These mutagenesis methods do not amplify the closed circular DNA, and they only mutate one of the two DNA strands in vitro. They are generally laborious, time-consuming, and with low mutation rates. The QuickChange™ method of Stratagene (La Jolla, Calif., catalog No. 200518) uses two complementary mutagenic primers and a thermostable polymerase to generate a mutated and nicked plasmid by thermal cycling. This method differs from LDA in that it does not include a thermostable DNA ligase in the reaction to seal the nick to generate a closed circular plasmid. Because the mutated strands are not covalently closed, they are not used as templates for exponential amplification. The two mutated strands have to be copied from the intact native DNA strands and then annealed to each other to form the mutated plasmid. Therefore, the yield of mutated plasmid is low. Also unlike LDA, QuickChange™ cannot be used to introduce multiple mutation sites simultaneously, and each mutation requires two mutagenic primers that have a complementary mutated sequence.

Besides its application for mutagenesis, the present method, by virtue of the use of sequence-specific primers to amplify closed circular DNA, also has, but should not be limited to, the following applications. (1) To selected and amplify a plasmid having an insert in the desired orientation in a ligation mixture. Plasmids with unwanted insert orientation will not be amplified. (2) To identify a desired plasmid clone by directly amplifying it from the transformed bacterial colonies in an agar plate. Plasmids without the cloned sequence will not be amplified. Therefore, LDA clonal screening will not require the time-consuming procedures, such as liquid culture, plasmid isolation, restriction mapping, and sequencing. (3) To detect point mutations in a closed circular DNA. The use of a primer with a single mismatched nucleotide at its 5' end will allow the correspondingly mutated DNA to be ligated, amplified, and thus identified. (4) To prepare closed circular DNA containing modified nucleotides, either randomly incorporated in both DNA strands or at a specific site or sites by the use of a primer or primers containing the modified nucleotides. These modified DNA molecules can be useful in studying DNA-DNA and DNA-protein interactions. (5) To isolate and amplify vectors carrying a gene or sequence of interest from genomic or cDNA libraries. This LDA library screening method greatly simplifies the gene hunting efforts. Targeted clones can be quickly isolated and analyzed. (6) To isolate and amplify closed circular viral DNA from infected cells or tissues for diagnosis and characterization. (7) To safely maintain and produce replicatively competent DNA, including viral DNA, in cell-free systems. This approach may be particularly useful to maintain DNA of interest without requiring sophisticated cell culture system. (8) To convert linear DNA molecules into closed circular DNA molecules. With the use of a primer that is complementary to both ends of a linear DNA in an LDA rection, the linear DNA can be converted into circular form and amplified. (9) To convert and amplify closed circular RNA molecules into their complementary DNA counterparts. This may be done with the use of a reverse transcriptase to copy the RNA into DNA prior to or during LDA amplification.

EXAMPLE 1

Figure 2:
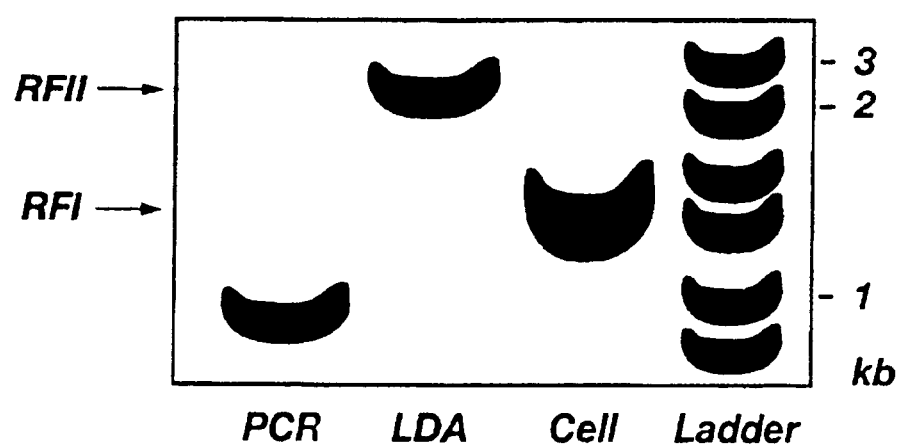
FIG. 2 shows electrophoretic separation of a 1990 bp plasmid DNA amplified by the present invention (LDA) and PCR (PCR) as compared to the same plasmid DNA isolated from a bacterial culture (Cell) and size markers (Ladder); RFI indicates supercoiled DNA, and RFII indicates closed circular DNA.

To demonstrate the feasibility of using LDA to generate and amplify closed circular DNA, two 5'-phosphorylated primers (a 16 mer and a 17 mer) were used to mutate and amplify a circular 1990 bp plasmid. The primers were complementary to different strands of the plasmid in an inward orientation, i.e., the 3' termini of the primers on different strands point to each other (FIG. 1) One of the primers (open arrow) possessed a single G to A mismatch on an HphI restriction site in the bleomycin resistance gene of the plasmid. The reaction mixture (50 μl) contained 10 ng of the native plasmid, 10 pmol of each primer, 10 nmol of the four dNTPs, 5 nmol of ATP, 2.5 units of $Pfu$ DNA polymerase (Stratagene, La Jolla, Calif.), 4 units of $Pfu$ DNA ligase (Stratagene), in 1×$Pfu$ DNA polymerase reaction buffer (20 mM Tris-HCl (pH 8.8), 10 mM KCl, 10 mM $(NH_4)_2SO_4$, 2 mM $MgSO_4$, 1% Triton X-100, and 100 μg/ml bovine serum albumin). The mixture was pre-incubated at 70° C. for 10 minutes to allow the ligase to repair any nick in the template. The mixture was then subjected to thermal cycling at 95° C. for 1 sec (denaturation), 50° C. for 1 sec (annealing), 72° C. for 4 min (extension), 95° C. for 1 sec (denaturation), and 72° C. for 4 min (annealing, extension, and ligation) for 20 cycles. This process favors the generation of full-length plasmid strands and formation of closed circular plasmid DNA. A control PCR was performed under similar conditions except that $Pfu$ DNA ligase was not included in the reaction mixture. The LDA and PCR products were analyzed by agarose gel electrophoresis along with the native plasmid directly isolated from bacterial culture. As shown in FIG. 2, including of $Pfu$ DNA ligase in the reaction, i.e. LDA, produced closed circular plasmid DNA that migrated in the gel slightly faster than the relaxed form (RFII), but slower than the supercoiled form (RFI) of the plasmid directly isolated from bacterial culture in contrast, in the absence of $Pfu$ DNA ligase, i.e. PCR, no circular plasmid DNA was generated.

EXAMPLE 2

Figure 3:
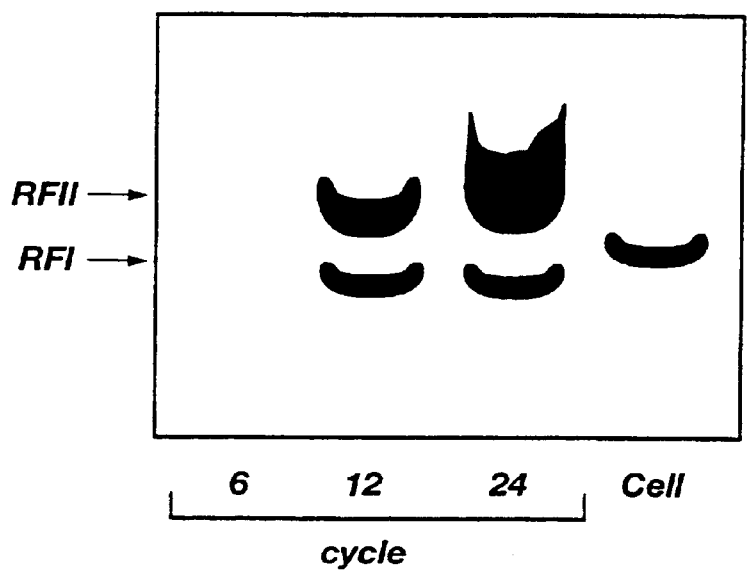
FIG. 3 shows electrophoretic separation of a 1990 bp plasmid DNA amplified by the present invention after 6, 12, and 24 cycles as compared to the same plasmid DNA isolated from a bacterial culture (Cell), RFI indicates supercoiled DNA, and RFII indicates closed circular DNA.

To demonstrate the amplification of closed circular DNA as a function of LDA cycle number, the procedure of Example 1 was followed except that LDA reactions were carried out for 6, 12, and 24 cycles. As shown in FIG. 3, the plasmid yield increases as the number of LDA cycles increases.

EXAMPLE 3

To demonstrate the functional competence of the LDA product, the amplified plasmids prepared according to the procedure of Example 1 were used to transform $E.\ coli$ DH5α, a non-mutS bacterial strain. The LDA-amplified plasmid was first digested with DpnI restriction enzyme to remove the starting template DNA. DpnI digests DNA only when its recognition site (5'-GATC-3') is methylated, and thus the original template DNA, but not in vitro amplified DNA, is digested. After DpnI digestion, the amplified DNA was introduced into $E.\ coli$ strain DH5α by electroporation. Analysis of ten randomly picked transformants showed that all clones had the desired mutation.

The results of Examples 1–3 demonstrate the ease of using LDA to introduce site-directed mutations in closed circular plasmid DNA and the feasibility of using LDA to amplify closed circular DNA with a specified sequence in vitro in a cell free system.

EXAMPLE 4

This example demonstrates that the present invention can be used to introduce multiple mutations simultaneously in a closed circular DNA. Three phosphorylated mutagenic primers complementary to the BsgI, BpmI, and BsmI sites in the large T antigen gene of BK virus in a plasmid of 5192 bp were used in an LDA reaction. The BsgI primer was complementary to one of the DNA strands, and the BpmI and BsmI primers to the other strand in an outward orientation, i.e. the 3' termini of the primers on different strands of the plasmid point away from each other. The reaction mixture (50 μl) contained 50 ng of the plasmid, 20 pmol of each primer, 10 nmol of dNTPs, 5 nmol of ATP, 2.5 units of $Pfu$ DNA polmerase (Stratagene), 4 units of $Pfu$ DNA ligase (Stratagene), in 1×$Pfu$ DNA polymerase reaction buffer. After an initial 10 minutes of 95° C. of denaturation, the mixture was subjected to 15 cycles of thermal cycling at 50° C. for 1 min, 72° C. for 8 min, 95° C. for 1 min, 72° C. for 8 min, and 95° C. for 1 min. After LDA amplification, the reaction mixture was digested with the restriction enzyme DpnI to remove the methylated native plasmid and then electroporated into *E. coli* DH5α. Clonal analysis showed that of ten clones tested, all lost the BsgI site, 8 clones also lost the BpmI site, and 6 clones lost all three restriction sites. These results demonstrate that LDA can be conveniently used to introduce multiple mutations simultaneously in a closed circular DNA.

EXAMPLE 5

Figure 4:
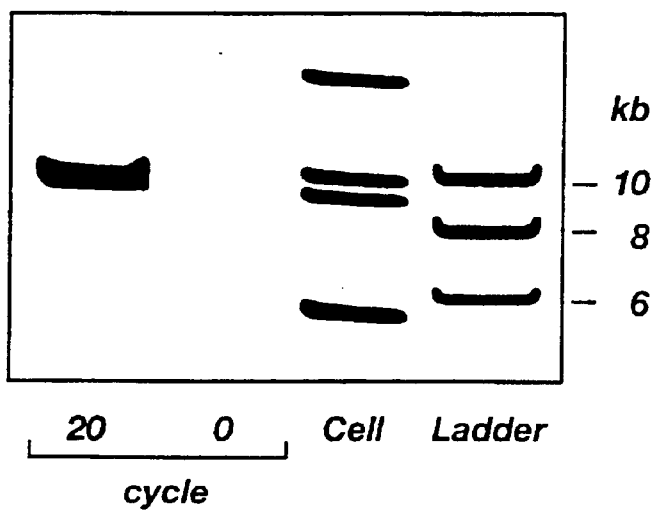
FIG. 4 shows electrophoretic separation of a 9516 bp plasmid DNA amplified by the procecure of the present invention after 0 and 20 cycles as compared to the same plasmid DNA isolated from a bacterial culture (Cell) and size markers (Ladder).

This example demonstrates that LDA can be used to amplify large closed circular DNAs. The sizes of most plasmid vectors used in molecular cloning are under 10,000 bp. In this example, a 9516 bp plasmid was amplified by LDA. The reaction conditions used were similar to those described in Example 1 except that the cycling conditions used were 94° C. for 10 sec, 50° C. for 2 min, 72° C. for 10 min, 94° C. for 10 sec, and 72° C. for to accomodate the larger size of the plasmid. Similar to the amplification of smaller plasmids, this large plasmid can also be amplified by LDA (FIG. 4). This result indicates that LDA should be applicable to the amplification of plasmid vectors commonly used in molecular cloning.

EXAMPLE 6

This example demonstrates that various thermostable DNA polymerases and thermostable ligases can be used for LDA amplification. The following combinations of thermostable DNA polymerase and DNA ligase were examined in LDA reactions: (1) *Pfu* DNA polymerase (Stratagene) and *Pfu* DNA ligase (Stratagene), (2) *Pfu* DNA polymerase (Stratagene) and AMPLIGASE® (a thermostable DNA ligase, Epicentre Technologies, Madison, Wis.), (3) ELONGASE™ (a mixture of *Taq* DNA polymerase and Pyrococcus species GB-D thermostable DNA polymerase, Life Technologies, Gaithersburg, Md.) and AMPLIGASE®, (4) VENT® DNA polymerase (*Thermococcus liloralis* DNA polymerase, F. Perler et al., 89 Proc. Nat'l Acad. Sci. USA 5577 (1992), New England Biolabs, Beverly, Mass.) and AMPLIGASE®, (5) BIO-X-ACT™ (a mixture of thermostable DNA polymerases, Intermountain Scientific Co., Kaysville, Utah) and *Pfu* DNA ligase (Stratagene). When LDA was performed using *Pfu* DNA ligase, the reaction buffers used were those of the DNA polymerases supplemented with ATP, which is a cofactor of the ligase. When AMPLIGASE® was used in the LDA reaction, the reaction buffers consisted of a 1:1 mix of the polymerase and ligase buffers supplied by the manufacturers. AMPLIGASE® uses β-NAD as a cofactor and is inhibited by ATP, therefore, the phosphorylated primers used in the LDA reaction must be purified free of ATP. Alternatively, the primers used in LDA can be phosphorylated chemically in the DNA synthesizer. All of these enzyme combinations worked well in LDA reactions for amplifying closed circular plasmids. The combination of BIO-X-ACT™ DNA polymerase and *Pfu* DNA ligase produced the highest yield of LDA product, and the expected closed circular DNA was the sole product as observed by gel electrophoresis. These results indicate that various thermostable DNA polymerases and ligases can be used in LDA reaction to produce and amplify closed circular DNA.

EXAMPLE 7

As shown in previous examples, it has been determined that the inclusion of an annealing step (e.g. incubation at about 72° C.) immediately following a denaturation step (e.g. incubation at about 95° C.) is important for the amplification of closed circular DNA. This sequence of steps inhibits the annealing of the input primers and instead allows the two strands of the standard PCR product (e.g. a 68 bp fragment in the illustration of FIG. 1) to anneal to the template and serve as megaprimers, S. H. Ke & E. L. Madison, 25 Nucl. Acids Res. 3371–72 (1997), for the LDA reaction. This prevents accumulation of the standard PCR product (i.e. the product defined by the 5' ends of the two primers), and favors amplification of the entire circular molecule. In fact, if the presently disclosed thermal cycling protocol is used, circular DNA can be amplified using either inward or outward primer orientations that are tens to thousands of base pairs apart. In the present example, a 1990 base pair plasmid was amplified according to the procedure of Example 1 except that the two 20-nucleotide, 5'-phosphorylated primers were designed to have 10 complementary nucleotides at their 5' ends, 10 and the thermal cycling protocol involved only two steps, a 95° C. denaturation step followed by a 68° C. extension and ligation step. The results were substantially similar to those of Example 1.

EXAMPLE 8

In this example, a mixture of a wild type plasmid and a mutant plasmid that differs from the wild type plasmid by a single point mutation is prepared with the wild type plasmid in large excess. 5'-Phosphorylated primers are designed such that one of the primers has its 5' nucleotide complementary to the nucleotide at the point mutation, whereas this primer has a mismatch with the wild type plasmid at the corresponding nucleotide residue. The mixture of plasmids is processed according to the procedure of Example 1, resulting in the selective amplification of the mutant plasmid and the lack of amplification of the wild type plasmid. This example shows that LDA can be used to detectpoint mutations.

EXAMPLE 9

In this example, the procedure of Example 1 is followed except that a mixture of [α-$^{35}$S]dATPαS and dATP is substituted for dATP. The resulting amplified closed circular plasmids contain the modified nucleotide, which shows that LDA can be used to amplify plasmids containing modified nucleotides that are incorporated randomly.

EXAMPLE 10

In this example, the procedure of Example 1 is followed except that the primers are prepared using [α-$^{35}$S]dATPαS instead of DATP. The resulting amplified closed circular plasmids contain the modified nucleotide, which shows that modified nucleotides can be introduced at selected sites.

EXAMPLE 11

In this example, the procedure of Example 1 is followed except that the template DNA is a mixture of DNAs prepared from a human genomic library, and the primers are designed for amplifying the β-actin gene. The resulting amplified closed circular DNA contains the β-actin gene. This shows that LDA can be used for amplifying a gene of interest from a genomic or cDNA library without the need for screening according to the standard methods of colony or plaque hybridization.

EXAMPLE 12

In this example, the procedure of Example 1 is followed except that the template is purified SV40 DNA, and the primers are designed for amplifying such SV40 DNA. The resulting amplified DNA is covalently closed circular SV40 DNA. This shows that LDA can be used to safely produce replicatively competent DNA, including viral DNA, in a cell-free system.

EXAMPLE 13

In this example, the procedure of Example 1 is followed except that the template is a mixture of plasmids having the β-actin gene cloned in both possible orientations in pBR322, and the primers are selected, by spanning the cloning sites, for selectively amplifying the gene in only one orientation. The resulting amplified closed circular DNA contains the β-actin gene in the selected orientation. This shows that LDA can be used to selectively amplify a gene cloned in a selected orientation.

EXAMPLE 14

In this example, plasmid pBR322 is amplified according to the procedure of Example 1 using 5'-phosphorylated primers, SEQ ID NO:1 and SEQ ID NO:2. The resulting amplified DNA is closed circular DNA.

(iv) a temperature suitable for thermostable DNA ligase-catalyzed closing of the extended primers, to result in an amplified closed circular DNA product.

2. The method of claim 1 wherein said closed circular nucleic acid is DNA.

3. The method of claim 1 wherein said temperature suitable for thermostable DNA polymerase-catalyzed extension of the primers is the same as the temperature suitable for thermostable DNA ligase-catalyzed closing of the extended primers.

4. The method of claim 3 wherein the temperature suitable for annealing the primers to the denatured template is the same as the temperature suitable for thermostable DNA polymerase-catalyzed extension of the primers.

5. The method of claim 1 wherein the LDA mixture is held at the temperature suitable for denaturing the template for about 1 second to about 2 minutes in each cycle.

6. The method of claim 1 wherein the LDA mixture is held at the temperature suitable for annealing the primers to the denatured template for about 1 second to about 5 minutes in each cycle.

7. The method of claim 1 wherein the LDA mixture is held at the temperature suitable for thermostable DNA

---

---

We claim:

1. A method for in vitro amplification of a selected closed circular nucleic acid comprising:
   (a) mixing a thermostable DNA ligase with a PCR reaction mixture comprising the selected closed circular nucleic acid as a template, a pair of 5'-phosphorylated PCR-amplification oligonucleotide primers, thermostable DNA polymerase, all four deoxyribonucleoside triphosphates, and an appropriate buffer comprising any cofactor required for activity of the thermostable DNA ligase, to result in an LDA mixture; and
   (b) thermocycling said LDA mixture through a selected number of cycles of
      (i) a temperature suitable for denaturing the template,
      (ii) a temperature suitable for annealing the primers to the denatured template,
      (iii) a temperature suitable for thermostable DNA polymerase-catalyzed extension of the primers, and polymerase-catalyzed extension of the primers for about 1 to 20 minutes in each cycle.

8. The method of claim 1 wherein at least one of the primers has at least one mismatch with its corresponding template strand, thus resulting in amplification of a mutated closed circular DNA product.

9. The method of claim 1, wherein the selected closed circular DNA comprises a chimera of an insert and a cloning vector such that the selected closed circular DNA includes two insert/vector recombination sites, wherein at least one of the primers hybridizes to its corresponding template strand across one of said two insert/vector recombination sites such that only one orientation of said insert in said cloning vector is amplified.

10. The method of claim 1 wherein the PCR reaction mixture further comprises a modified deoxyribonucleoside triphosphate such that a corresponding modified nucleotide is randomly incorporated into the amplified closed circular DNA product.

11. The method of claim 1 wherein at least one of the primers comprises a modified nucleotide such that the modified nucleotide is site-specifically incorporated into the amplified closed circular DNA product.

12. The method of claim 1 wherein one of said pair of 5'-phosphorylated amplification primers is mismatched at its 5'-end with a corresponding nucleotide of the selected closed circular DNA such that only closed circular DNA mutated at the corresponding nucleotide to base pair at the 5'-end of said one of said pair of 5'-phosphorylated amplication primers is amplified.

13. The method of claim 1 wherein said selected closed circular DNA is replicatively competent DNA.

14. The method of claim 13 wherein said replicatively competent DNA is a viral DNA.

15. The method of claim 1 wherein said closed circular nucleic acid is RNA and said thermostable DNA polymerase is a reverse transcriptase.

16. A method of converting a linear nucleic acid to a circular form thereof comprising:
  (a) mixing a thermostable DNA ligase with a PCR reaction mixture comprising the selected linear nucleic acid as a template, a pair of 5'-phosphorylated PCR-amplification oligonucleotide primers wherein one of said pair of 5'-phosphorylated PCR-amplification oligonucleotide primers hybridizes to both the 5'-end and the 3'-end of said linear nucleic acid, thermostable DNA polymerase, all four deoxyribonucleoside triphosphates, and an appropriate buffer comprising any cofactor required for activity of the thermostable DNA ligase, to result in an LDA mixture; and
  (b) thermocycling said LDA mixture through a selected number of cycles of
    (i) a temperature suitable for denaturing the template,
    (ii) a temperature suitable for annealing the primers to the denatured template,
    (iii) a temperature suitable for thermostable DNA polymerase-catalyzed extension of the primers, and
    (iv) a temperature suitable for thermostable DNA ligase-catalyzed closing of the extended primers, to result in an amplified closed circular DNA form of said linear nucleic acid.

17. The method of claim 16 wherein said linear nucleic acid is DNA.

18. The method of claim 16 wherein said temperature suitable for thermostable DNA polymerase-catalyzed extension of the primers is the same as the temperature suitable for thermostable DNA ligase-catalyzed closing of the extended primers.

19. The method of claims 18 wherein the temperature suitable for annealing the primers to the denatured template is the same as the temperature suitable for thermostable DNA polymerase-catalyzed extension of the primers.

20. The method of claim 16 wherein the LDA mixture is held at the temperature suitable for denaturing the template for about 1 second to about 2 minutes in each cycle.

21. The method of claim 16 wherein the LDA mixture is held at the temperature suitable for annealing the primers to the denatured template for about 1 second to about 5 minutes in each cycle.

22. The method of claim 16 wherein the LDA mixture is held at the temperature suitable for thermostable DNA polymerase-catalyzed extension of the primers for about 1 to 20 minutes in each cycle.

23. The method of claim 16 wherein at least one of the primers has at least one mismatch with its corresponding template strand, thus resulting in amplification of a mutated closed circular DNA product.

24. The method of claim 16 wherein the PCR reaction mixture further comprises a modified deoxyribonucleoside triphosphate such that a corresponding modified nucleotide is randomly incorporated into the amplified closed circular DNA product.

25. The method of claim 16 wherein at least one of the primers comprises a modified nucleotide such that the modified nucleotide is site-specifically incorporated into the amplified closed circular DNA product.

26. The method of claim 16 wherein one of said pair of 5'-phosphorylated amplification primers is mismatched at its 5'-end with a corresponding nucleotide of the linear nucleic acid such that only linear nucleic acid mutated at the corresponding nucleotide to base pair at the 5'-end of said one of said pair of 5'-phosphorylated amplication primers is amplified.

27. The method of claim 16 wherein said linear nucleic acid is replicatively competent DNA.

28. The method of claim 27 wherein said replicatively competent DNA is a viral DNA.

29. The method of claim 16 wherein said linear nucleic acid is RNA and said thermostable DNA polymerase is a reverse transcriptase.

* * * * *